(12) United States Patent
Konno et al.

(10) Patent No.: US 11,304,602 B2
(45) Date of Patent: Apr. 19, 2022

(54) PULSE PHOTOMETRY PROBE

(71) Applicant: NIHON KOHDEN CORPORATION, Tokyo (JP)

(72) Inventors: Norihito Konno, Tokorozawa (JP); Junichi Sato, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 626 days.

(21) Appl. No.: 16/120,853

(22) Filed: Sep. 4, 2018

(65) Prior Publication Data

US 2019/0090745 A1    Mar. 28, 2019

(30) Foreign Application Priority Data

Sep. 26, 2017  (JP) .............................. JP2017-184783

(51) Int. Cl.
*A61B 5/00* (2006.01)
*A61B 5/1455* (2006.01)

(52) U.S. Cl.
CPC ........ *A61B 5/0004* (2013.01); *A61B 5/14552* (2013.01); *A61B 5/6826* (2013.01); *A61B 2562/0238* (2013.01)

(58) Field of Classification Search
CPC ... A61B 5/004; A61B 5/1455; A61B 5/14552; A61B 5/6826; A61B 5/024; A61B 5/02416; A61B 5/02438; A61B 2562/0238
USPC .................................................. 600/344, 323
See application file for complete search history.

(56) References Cited

U.S. PATENT DOCUMENTS

| | | | |
|---|---|---|---|
| 8,761,852 B2 * | 6/2014 | Parthasarathy | .......... A61B 5/11 600/323 |
| 2007/0123756 A1 | 5/2007 | Kitajima et al. | |
| 2010/0210924 A1 | 8/2010 | Parthasarathy et al. | |
| 2014/0364705 A1 | 12/2014 | Parthasarathy et al. | |
| 2015/0208967 A1 * | 7/2015 | Tateda | ............... A61B 5/14552 600/324 |
| 2017/0086722 A1 | 3/2017 | Shigenaga et al. | |

FOREIGN PATENT DOCUMENTS

| | | |
|---|---|---|
| JP | 2007-105316 A | 4/2007 |
| JP | 2007-167183 A | 7/2007 |
| JP | 2012-517888 A | 8/2012 |
| WO | 2014-024653 A1 | 2/2014 |
| WO | 2015-141446 A1 | 9/2015 |

OTHER PUBLICATIONS

Japanese Office Action dated Apr. 13, 2021 issued in Japanese Patent Application No. 2017-184783.

* cited by examiner

*Primary Examiner* — Daniel L Cerioni
*Assistant Examiner* — Deirdre M Willgohs
(74) *Attorney, Agent, or Firm* — Pearne & Gordon LLP

(57) ABSTRACT

A pulse photometry probe which is to be attached to a living tissue of a subject includes a light emitter that emits a light beam toward the living tissue of the patient, a light detector that receives the light beam emitted from the light emitter and passing through the living tissue, to produce a vital signal, a vital data acquiring section that acquires vital data of the patient based on the vital signal, and a wireless communicating section that wirelessly transmits the vital data.

16 Claims, 7 Drawing Sheets

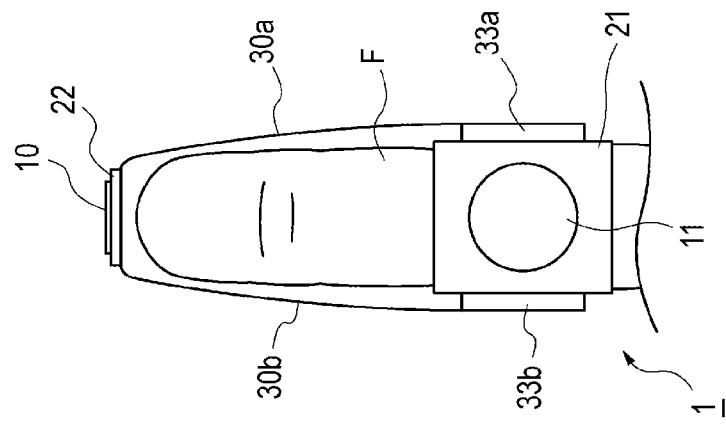
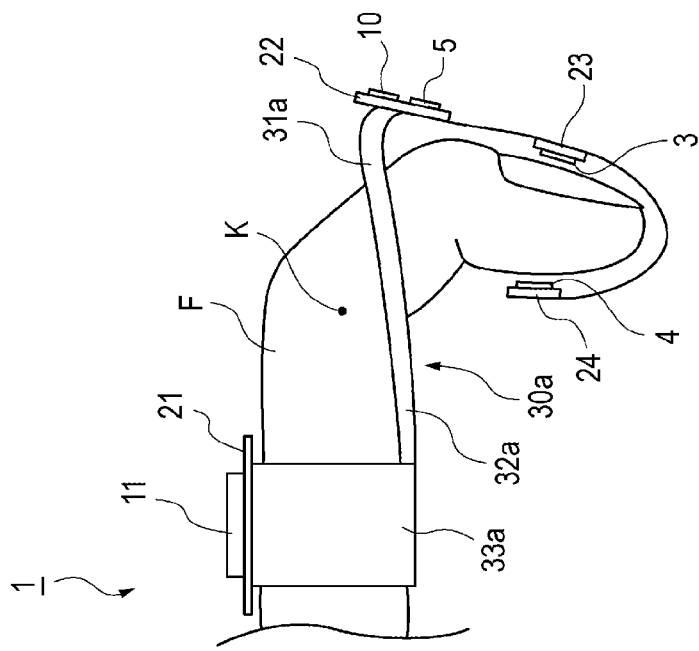

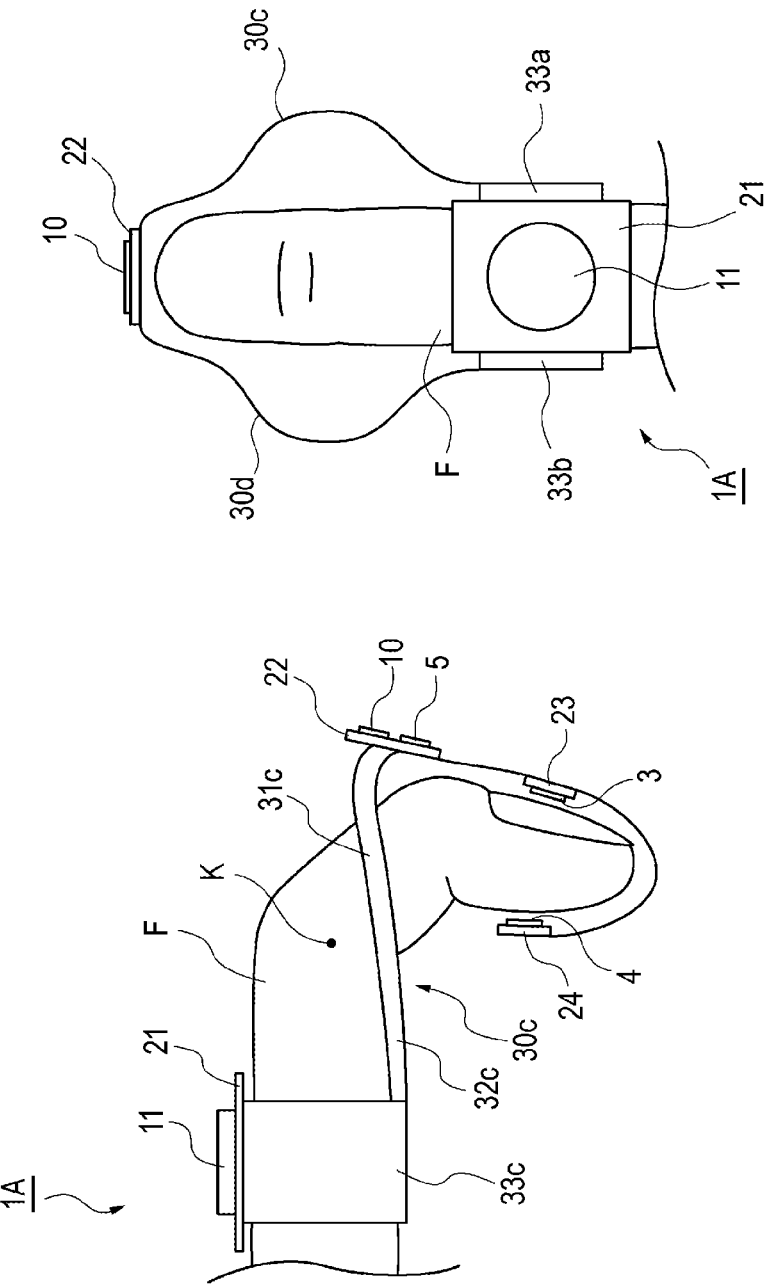

PULSE PHOTOMETRY PROBE

CROSS REFERENCE TO RELATED APPLICATION

This application is based on Japanese Patent Applications No. 2017-184783 filed on Sep. 26, 2017, the contents of which are incorporated herein by reference.

BACKGROUND

The presently disclosed subject matter relates to a pulse photometry probe.

JP-A-2007-167183 discloses a pulse oximeter in which a probe is to be attached to the finger or the like of the patient, and which can then measure vital signs information of the patient (such as the arterial oxygen saturation (SpO2) and the pulse rate). According to the disclosure of JP-A-2007-167183, the probe including a light emitter and a light detector is attached to the finger of the patient, and the main unit of the pulse oximeter acquires pulse wave data and SpO2 data of the patient based on electrical signals obtained from the light detector.

The measurement data such as the pulse wave data and the SpO2 data are transferred from the pulse oximeter main unit to a stationary personal computer (PC), and then the PC analyzes the transferred measurement data to estimate the health condition of the patient, or, based on the pulse wave data, renders the pulse wave on a display screen.

In the pulse oximeter disclosed in Patent Literature 1, when the vital signs information of the patient is to be measured, the movement of the patient is limited. Particularly, the probe is connected to the pulse oximeter main unit through a probe cable, and, while the vital signs information of the patient is measured, the probe cable therefore blocks the patient from freely moving in the hospital. Moreover, the place where the vital signs information of the patient can be measured is limited to the hospital. It may be contemplated that the patient may move in the hospital while always carrying the probe and the pulse oximeter main unit. In this case, however, the pulse oximeter main unit and the probe cable impede the movement of the patient.

A pulse photometry probe which has improved usability is provided.

SUMMARY

According to an aspect of the presently disclosed subject matter, a pulse photometry probe which is to be attached to a living tissue of a subject, includes:

a light emitter that emits a light beam toward the living tissue of the patient;

a light detector that receives the light beam emitted from the light emitter and passing through the living tissue, to produce a vital signal;

a vital data acquiring section that acquires vital data of the patient based on the vital signal; and a wireless communicating section that wirelessly transmit the vital data.

According to the presently disclosed subject matter, it is possible to provide a pulse photometry probe which has improved usability.

BRIEF DESCRIPTION OF DRAWINGS

FIG. 5A is a view of the probe circuit section in a state where the finger is bent, as seen from the lateral side, and FIG. 5B is a view of the probe circuit section illustrated in FIG. 5A, as seen from the upper side.

FIG. 7A is a view of the probe circuit section in a state where the finger is bent, as seen from the lateral side, and FIG. 7B is a view of the probe circuit section illustrated in FIG. 7A, as seen from the upper side.

DETAILED DESCRIPTION OF EMBODIMENTS

Figure 1:
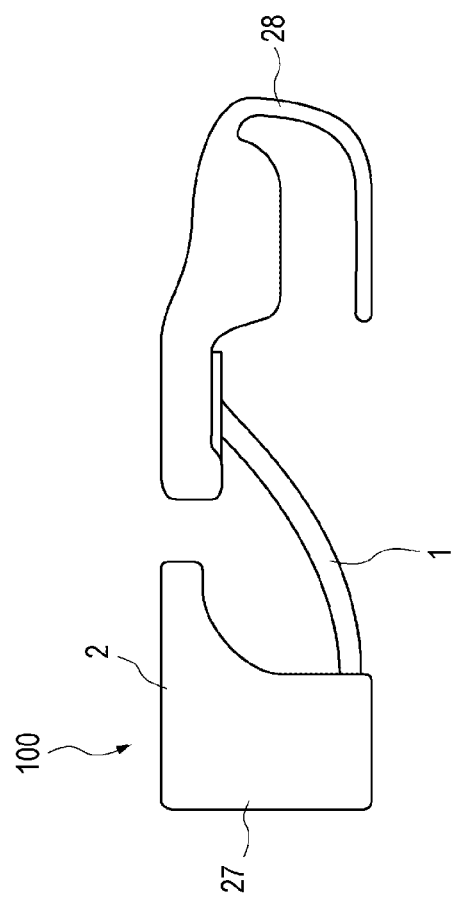
FIG. 1 is a view illustrating the appearance of a probe of an embodiment of the invention (hereinafter, referred to simply as the embodiment).

Hereinafter, an embodiment of the invention (hereinafter, referred to simply as the embodiment) will be described with reference to the drawings. In the description of the embodiment, description of components which are denoted by the same reference numerals as those designating components that have been already described will be omitted for the sake of convenience in description. The dimensions of components illustrated in the drawings may be sometimes different from the actual dimensions of the components for the sake of convenience in description.

FIG. 1 is a view illustrating the appearance of a pulse photometry probe 100 (hereinafter, referred to simply as the probe 100) of the embodiment. As illustrated in FIG. 1, the probe 100 includes a probe circuit section 1 and a cover 2 which is configured so as to cover the probe circuit section 1. For example, the probe 100 is a probe for a pulse oximeter. The configuration of the probe circuit section 1 will be described later. The cover 2 is disposed in order to protect the probe circuit section 1 from an external impact, and has an insertion port 27 through which the finger (an example of the living tissue of the patient) of the patient (subject) is to be inserted. When the finger of the patient is inserted through the insertion port 27, the probe 100 is attached to the finger. In a state where the probe 100 is attached to the finger, a tip end portion 28 of the cover 2 butts against the tip end of the finger. The cover 2 is formed by, for example, a plastic material. In the embodiment, as illustrated in FIG. 1, a cable such as a probe cable is not connected to the probe 100.

Figure 2:
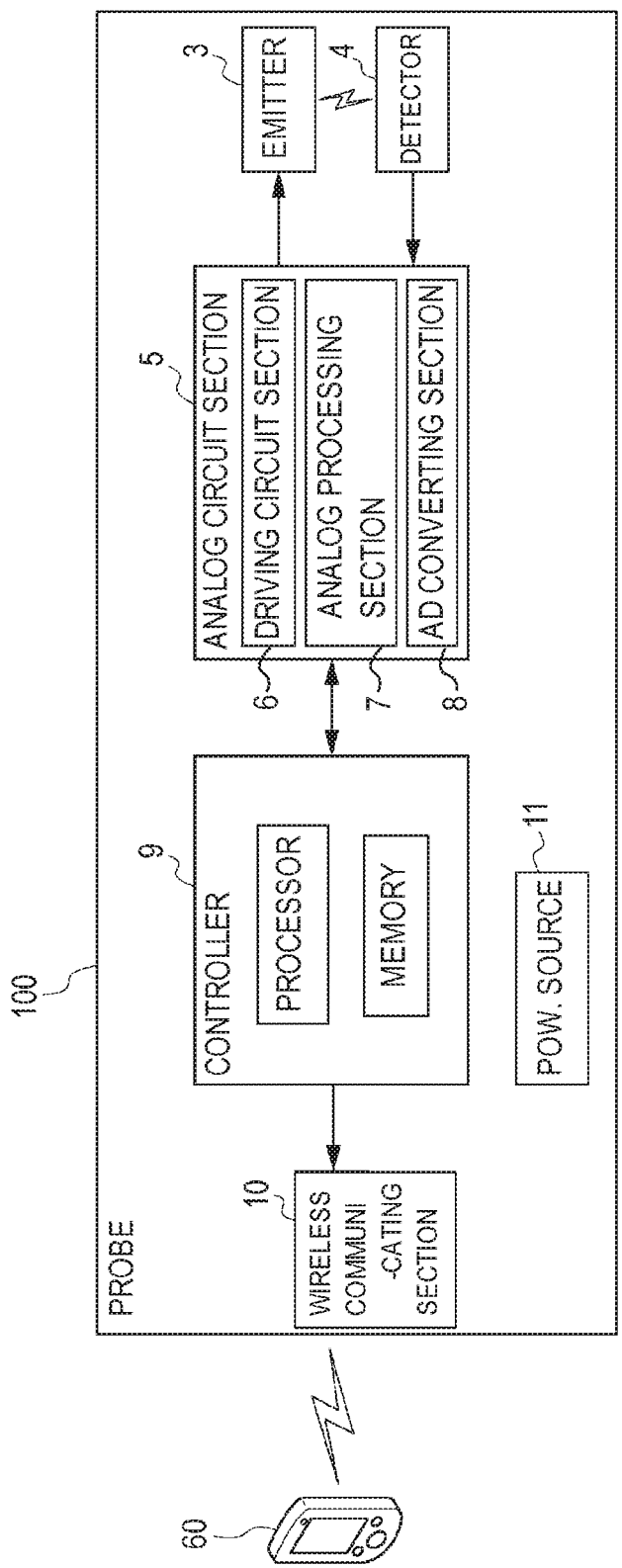
FIG. 2 is a diagram illustrating the hardware configuration of the probe of the embodiment.

Next, the hardware configuration of the probe 100 (specifically, the probe circuit section 1) will be described with reference to FIG. 2. FIG. 2 is a diagram illustrating the hardware configuration of the probe 100 (specifically, the probe circuit section 1). As illustrated in FIG. 2, the probe 100 includes a light emitter 3, a light detector 4, an analog circuit section 5, a controller 9, a wireless communicating section 10, and a power source section 11.

The light emitter 3 is configured so as to emit a light beam toward the finger of the patient, and, for example, an LED (Light Emitting Diode). In the case where the probe 100 functions as a pulse oximeter, the light emitter 3 has a red LED which is configured so as to emit a red light beam, and an infrared LED which is configured so as to emit an infrared light beam. The red LED and the infrared LED are driven and controlled so as to alternately emit respective light beams. When a pulse current which is supplied to the infrared LED is at a high level, for example, a pulse current which is supplied to the red LED is at a low level. By contrast, when the pulse current which is supplied to the infrared LED is at a low level, the pulse current which is supplied to the red LED is at a high level.

The light detector 4 is configured so as to receive the light beam which is emitted from the light emitter 3, and which passes through the finger of the patient, and produce a vital signal (electrical signal). For example, the light detector 4 is a photoelectric converting device such as a PD (Photodiode). The number of the light detector 4 is not particularly limited. In the case where the light emitter 3 has a red LED and an infrared LED, for example, the light detector 4 has a photosensitivity to a red light beam emitted from the red LED, and an infrared light beam emitted from the infrared LED.

A red light beam is not well absorbed by oxyhemoglobin (HbO2) which is contained in the blood flowing through a blood vessel in the finger. By contrast, a red light beam is well absorbed by hemoglobin (Hb) which is contained in the blood. In the case where the blood contains much oxyhemoglobin, a large amount of the red light beam passes through the finger, and then is received by the light detector 4. On the contrary, in the case where the blood does not contain much oxyhemoglobin, the intensity of the red light beam received by the light detector 4 is reduced. As described above, the intensity of the red light beam which is received by the light detector 4 is changed in accordance with the rate of oxyhemoglobin in the blood. On the other hand, an infrared light beam is not well absorbed by oxyhemoglobin and hemoglobin. More specifically, the extinction coefficient of an infrared light beam in oxyhemoglobin is not largely different from that of an infrared light beam in hemoglobin. Therefore, the SpO2 value of the patient can be calculated by using a ratio of the intensity of the red light beam which is received by the light detector 4, to that of the infrared light beam which is received by the light detector 4.

The analog circuit section 5 includes a driving circuit section 6, an analog processing section 7, and an AD (Analog to Digital) converting section 8. For example, the analog circuit section 5 may be configured as an AFE (Analog Front End) chip. The driving circuit section 6 is configured so as to control the driving current (pulse current) supplied to the light emitter 3, based on a control signal which is output from the controller 9. For example, the driving circuit section 6 is configured so as to control the timing of the pulse current supplied to the red LED, and that of the pulse current supplied to the infrared LED.

The analog processing section 7 is configured so as to amplify the vital signal (the electrical signal which is photoelectrically converted) output from the light detector 4, and filter out noise components (for example, high-frequency components) of the amplified vital signal. The AD converting section 8 is configured so as to convert the vital signal (analog signal) output from the analog processing section 7 to a digital signal, based on a control signal which is output from the controller 9. As described above, the vital signal output from the light detector 4 is converted to a digital signal by the analog circuit section 5.

The controller 9 has a processor and a memory. The processor is a CPU, a GPU, and/or an MPU. The memory includes a RAM and a ROM. The controller 9 receives the digital signal of the vital signal (hereinafter, referred to simply as the digital signal) from the AD converting section 8, and, by using a timer function of the processor, can acquire pulse wave data in which the digital signal and time information are associated with each other. The pulse wave data have information relating to the intensities of the light beams received by the light detector 4, and time information. The pulse wave data may include pulse wave data associated with the red light beam, and those associated with the infrared light beam. The pulse wave data may be stored in the RAM, or in a storage device such as a flash memory which is not illustrated.

Based on the produced pulse wave data, the controller 9 may further acquire SpO2 data indicating a temporal change of the SpO2 value, and/or pulse rate data indicating a temporal change of the pulse rate. The controller 9 can calculate the SpO2 data based on the pulse wave data associated with the red light beam, and those associated with the infrared light beam. As described above, the controller 9 can acquire pulse wave data, SpO2 data, and/or pulse rate data as vital data, based on the digital signal output from the AD converting section 8.

Although, in the embodiment, the controller 9 is configured by the memory and the processor, the controller 9 may be configured by an integrated circuit such as an ASIC or an FPGA. Alternatively, the controller 9 may be configured by a processor, a memory, and an integrated circuit such as an ASIC or an FPGA. The controller 9 and the AD converting section 8 function as the vital data acquiring section which acquires vital data (pulse wave data, SpO2 data, and/or pulse rate data) of the patient based on the vital signal.

The wireless communicating section 10 is configured so as to wirelessly transmit vital data (pulse wave data, SpO2 data, and/or pulse rate data). In the case where wireless communication between the wireless communicating section 10 and a communication terminal 60 has been established, for example, the wireless communicating section 10 can transmit vital data to the communication terminal 60. After receiving vital data from the probe 100, the communication terminal 60 may cause a trend graph indicating a temporal change of the vital data, and/or the numerical values of the vital signs information (the SpO2 value and the pulse rate) to be displayed on a display. The communication terminal 60 has a wireless communication function, and is, for example, a mobile telephone, a smart phone, a tablet, a personal computer, a wearable device such as an AR glass or a smart watch, or a patient monitor. For example, the standard of wireless communication between the wireless communicating section 10 and the communication terminal 60 is the Wi-Fi (registered trademark), the Bluetooth (registered trademark), the ZigBee (registered trademark), or the LPWA. The wireless communicating section 10 includes an antenna, a wireless transmitting circuit including a DA converting section, and a wireless receiving circuit including an AD converting section. Alternatively, the wireless communicating section 10 may transmit vital data to a server in a communication network such as the Internet.

The power source section 11 is electrically connected to the wireless communicating section 10, the controller 9, and the analog circuit section 5, and configured so as to supply electric power to these sections. For example, the power source section 11 is a coin cell, an energy harvest power source, a power source for wireless power supply, or a secondary cell. The coin cell is a lithium coin cell, an air zinc cell, or the like. In the energy harvest power source, electricity may be generated by solar power generation, vibration power generation, or temperature difference power generation. For example, the secondary cell is a card-type lithium-ion secondary cell or a thin cell.

According to the embodiment, vital data are acquired by the probe 100, the acquired vital data are wirelessly transmitted to the communication terminal 60, and therefore it is not required to connect the probe 100 to an external apparatus (for example, a personal computer or the main unit of the pulse oximeter) by using a wired cable. In the state where the probe 100 is attached to the finger, consequently, the patient can move comparatively freely inside or outside the hospital. Since the patient can move comparatively freely during a period when vital signs information (the SpO2 value and the like) is measured, moreover, vital signs information can be easily measured in everyday life. Therefore, the usability of the probe 100 can be improved.

In the probe 100, moreover, the vital signal output from the light detector 4 is converted to a digital signal, and vital data are acquired based on the vital signal which has been converted to the digital signal. In this way, vital data are acquired only by the probe 100, and therefore the usability of the probe 100 can be improved.

Figure 3:
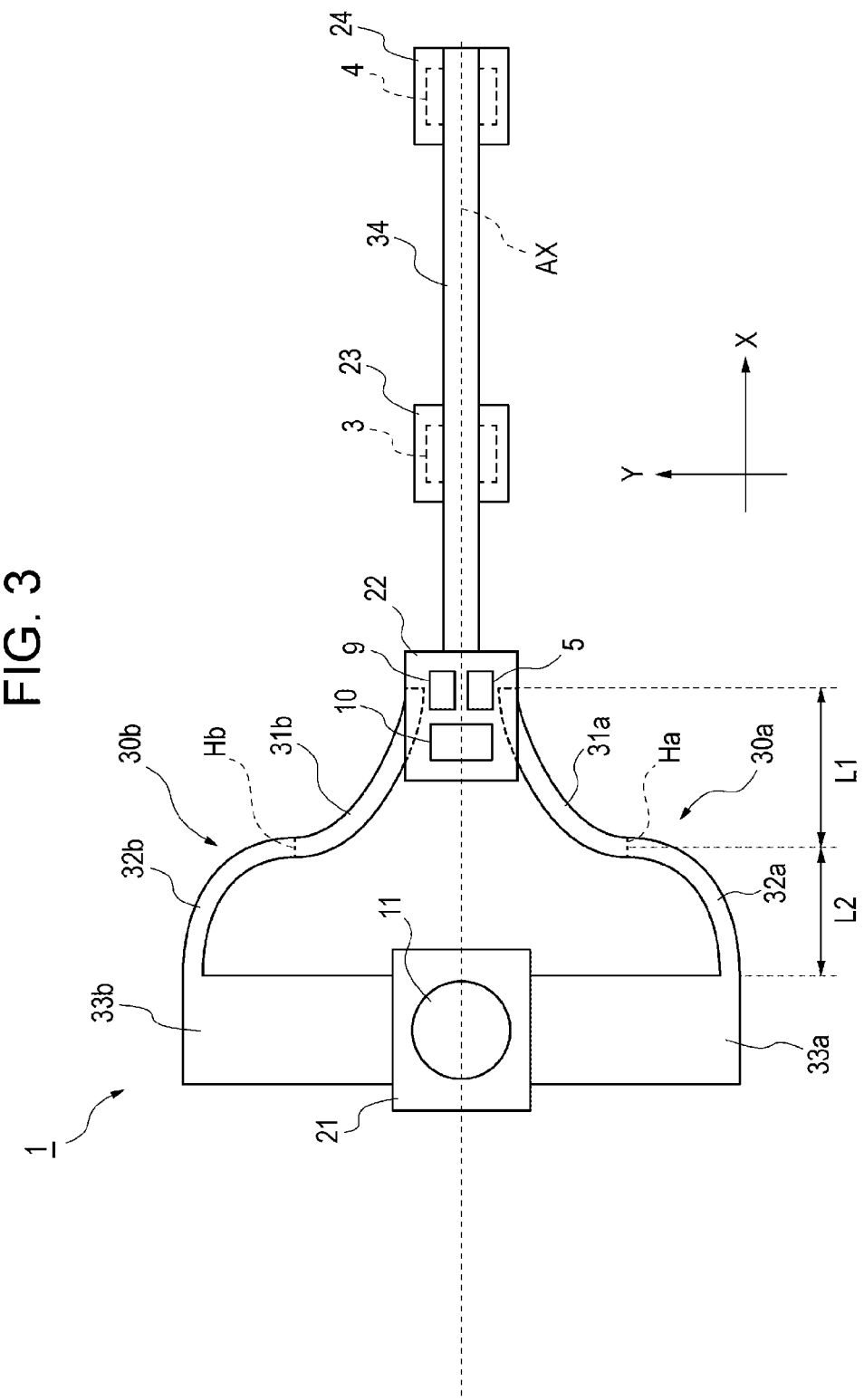
FIG. 3 is a development view of a probe circuit section.
Figure 4:
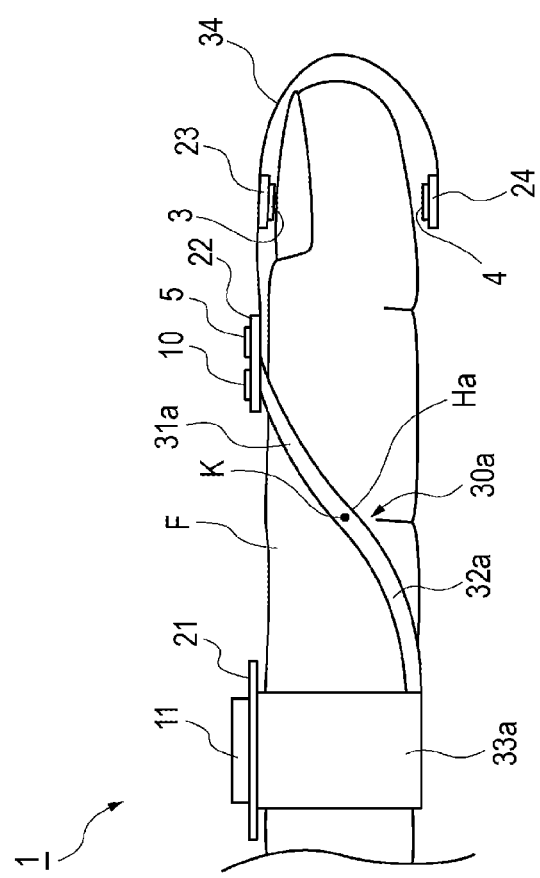
FIG. 4 is a view illustrating a state where the probe circuit section is attached to the finger of the patient.

Next, the configuration of the probe circuit section 1 of the probe 100 will be specifically described with reference to FIGS. 3 and 4. FIG. 3 is a development view of the probe circuit section 1, and FIG. 4 is a view illustrating a state where the probe circuit section 1 is attached to the finger F of the patient. In FIG. 4, for the sake of convenience in description, the illustration of the cover 2 is omitted.

As illustrated in FIG. 3, the probe circuit section 1 includes the light emitter 3, the light detector 4, the analog circuit section 5, the controller 9, the wireless communicating section 10, and the power source section 11. The probe circuit section 1 further includes a mounting portion 21 (the first mounting portion), a mounting portion 22 (the second mounting portion), a mounting portion 23 (the third mounting portion), and a mounting portion 24 (the fourth mounting portion), wherein the second, third, and fourth mounting portions 22-24 are movable relative to the first mounting portion 21 (see e.g., FIGS. 4 and 5A).

Each of the mounting portions 21 to 24 is configured by a flexible printed circuit board (FPC), a rigid circuit board, or the like. A flexible printed circuit board includes a board body which is made of an insulating material such as polyimide, and a wiring pattern which is formed on the board body, and which is made of a conductive material (for example, a copper foil). A rigid circuit board includes a board body which is made of an insulating material such as a glass-epoxy resin, and a wiring pattern which is formed on the board body, and which is made of a conductive material. Alternatively, one or more of the mounting portions 21 to 24 may be configured by a flexible printed circuit board(s), and the other(s) of the mounting portions 21 to 24 may be configured by a rigid circuit board(s).

The mounting portion 21 is configured so that the power source section 11 (for example, a coin cell) is mounted thereon. The power source section 11 is electrically connected to the wiring pattern of the mounting portion 21. The mounting portion 22 is configured so that the wireless communicating section 10, the analog circuit section 5, and the controller 9 are mounted thereon. The wireless communicating section 10, the analog circuit section 5, and the controller 9 are electrically connected to the wiring pattern of the mounting portion 22. Particularly, the wireless communicating section 10, the analog circuit section 5, and the controller 9 are electrically connected to one another through the wiring pattern of the mounting portion 22. The mounting portion 23 is configured so that the light emitter 3 is mounted thereon. The light emitter 3 is electrically connected to the wiring pattern of the mounting portion 23. The mounting portion 23 is configured so that the light detector 4 is mounted thereon. The light detector 4 is electrically connected to the wiring pattern of the mounting portion 24.

In a state where the probe circuit section 1 (the probe 100) is attached to the finger F of the patient, as illustrated in FIG. 4, the light emitter 3 is opposed to the light detector 4 through the finger F. Therefore, the light detector 4 can receive the light beam which is emitted from the light emitter 3, and which passes through the finger F.

Although, in the embodiment, the four mounting portions 21 to 24 are configured by the four respective individual circuit boards, the mounting portions may be configured by one to three circuit boards. For example, one flexible printed circuit board may function as the mounting portions 21 to 24.

The probe circuit section 1 further includes a first connecting portion 33a, a second connecting portion 33b, a third connecting portion 34, a first arm portion 30a, and a second arm portion 30b. Each of the first connecting portion 33a, the second connecting portion 33b, the third connecting portion 34, the first arm portion 30a, and the second arm portion 30b is configured by a flexible printed circuit board or a metal wire. Alternatively, at least one of these portions may be configured by a flexible printed circuit board, and the other(s) of the portions may be configured by a metal wire(s).

The first connecting portion 33a is connected physically and electrically to the mounting portion 21, and electrically connected to the power source section 11 through the mounting portion 21. The second connecting portion 33b is connected physically and electrically to the mounting portion 21, and electrically connected to the power source section 11 through the mounting portion 21. The third connecting portion 34 is connected physically and electrically to the mounting portions 22 to 24. The third connecting portion 34 is electrically connected to at least the analog circuit section 5 through the mounting portion 22. The third connecting portion 34 is electrically connected to the light emitter 3 through the mounting portion 23. The third connecting portion 34 is electrically connected to the light detector 4 through the mounting portion 24. In this way, the mounting portion 22 is electrically connected to the mounting portions 23, 24 through the third connecting portion 34. Specifically, the analog circuit section 5 is electrically connected to the light emitter 3 and the light detector 4 through the third connecting portion 34.

The first arm portion 30a is connected physically and electrically to the first connecting portion 33a and the mounting portion 22. As described above, the first arm portion 30a electrically connects the mounting portions 21, 22 to each other. The first arm portion 30a has a first arcuate portion 31a and a second arcuate portion 32a. The first arcuate portion 31a is arcuate toward the mounting portion 21, and connected to the mounting portion 22. The second arcuate portion 32a is arcuate so as to separate from the mounting portion 21, and connected to the first connecting portion 33a.

The first arcuate portion 31a is formed integrally with the second arcuate portion 32a. The borderline Ha between the first arcuate portion 31a and the second arcuate portion 32a is the inflection point of the curve of the first arm portion 30a. Preferably, the curvature of the first arcuate portion 31a coincides with that of the second arcuate portion 32a. In the insertion direction (the X-axis direction illustrated in FIG. 3) along which the finger F of the patient is to be inserted, the length L1 of the first arcuate portion 31a is equal to or longer than the length L2 of the second arcuate portion 32a (L1☐L2). As illustrated in FIG. 4, moreover, it is preferable that, in the state where the probe circuit section 1 is attached to the finger F, the borderline Ha approximately coincides with the center axis K of the proximal interphalangeal joint of the finger F.

The second arm portion 30b is disposed so as to be opposed to the first arm portion 30a in the Y-axis direction which is perpendicular to the X-axis direction (the insertion direction). Particularly, the first arm portion 30a and the second arm portion 30b are symmetrical with each other about an axis Ax. The axis Ax is parallel to the X-axis direction, and passes through the center of the mounting portion 22.

The second arm portion 30b is connected physically and electrically to the second connecting portion 33b and the mounting portion 22. As described above, the second arm portion 30b electrically connects the mounting portions 21, 22 to each other. The second arm portion 30b has a first arcuate portion 31b and a second arcuate portion 32b. The first arcuate portion 31b is arcuate toward the mounting portion 21, and connected to the mounting portion 22. The second arcuate portion 32b is arcuate so as to separate from the mounting portion 21, and connected to the second connecting portion 33b.

The first arcuate portion 31b is formed integrally with the second arcuate portion 32b. The borderline Hb between the first arcuate portion 31b and the second arcuate portion 32b is the inflection point of the curve of the second arm portion 30b. In the X-axis direction, the length of the first arcuate portion 31b is longer than that of the second arcuate portion 32b. Similarly with the first arm portion 30a, it is preferable that, in the state where the probe circuit section 1 is attached to the finger F, the borderline Hb approximately coincides with the center axis K of the proximal interphalangeal joint of the finger F.

Since the first arm portion 30a and the second arm portion 30b are disposed as described above, the electric power generated in the power source section 11 can be supplied to the analog circuit section 5, the controller 9, and the wireless communicating section 10. Moreover, the pair of arm portions (the first arm portion 30a and the second arm portion 30b) which are axisymmetric with each other are disposed, and therefore the design property of the probe 100 can be improved. Although, in the embodiment, the two arm portions are disposed, only one of the two arm portions may be disposed.

Next, the state of the probe circuit section 1 in the case where the finger F of the patient is bent will be described with reference to FIGS. 5A and 5B. FIG. 5A is a view of the probe circuit section 1 in a state where the finger F is bent, as seen from the lateral side, and FIG. 5B is a view of the probe circuit section 1 illustrated in FIG. 5A, as seen from the upper side. In FIGS. 5A and 5B, for the sake of convenience in description, the illustration of the cover 2 (see FIG. 1) is omitted.

As illustrated in FIG. 5B, even in the case where the distal and proximal interphalangeal joints of the finger F are bent, the first arm portion 30a and second arm portion 30b of the probe circuit section 1 do not largely expand toward the outside of the probe circuit section 1. As illustrated in FIG. 3, in the X-axis direction, namely, the length L1 of the first arcuate portion 31a is equal to or longer than the length L2 of the second arcuate portion 32a (L1☐L2), and therefore it is possible to prevent the first arm portion 30a from largely expanding so as to separate from the finger F, even in the case where the distal and proximal interphalangeal joints of the finger F are bent. In the X-axis direction, similarly, the length of the first arcuate portion 31b is longer than that of the second arcuate portion 32b, and therefore it is possible to prevent the second arm portion 30b from largely expanding so as to separate from the finger F, even in the case where the distal and proximal interphalangeal joints of the finger F are bent. Therefore, the two arm portions which largely expand can be preferably prevented from interfering with another article, and hence the usability of the probe 100 can be improved.

Figure 6:
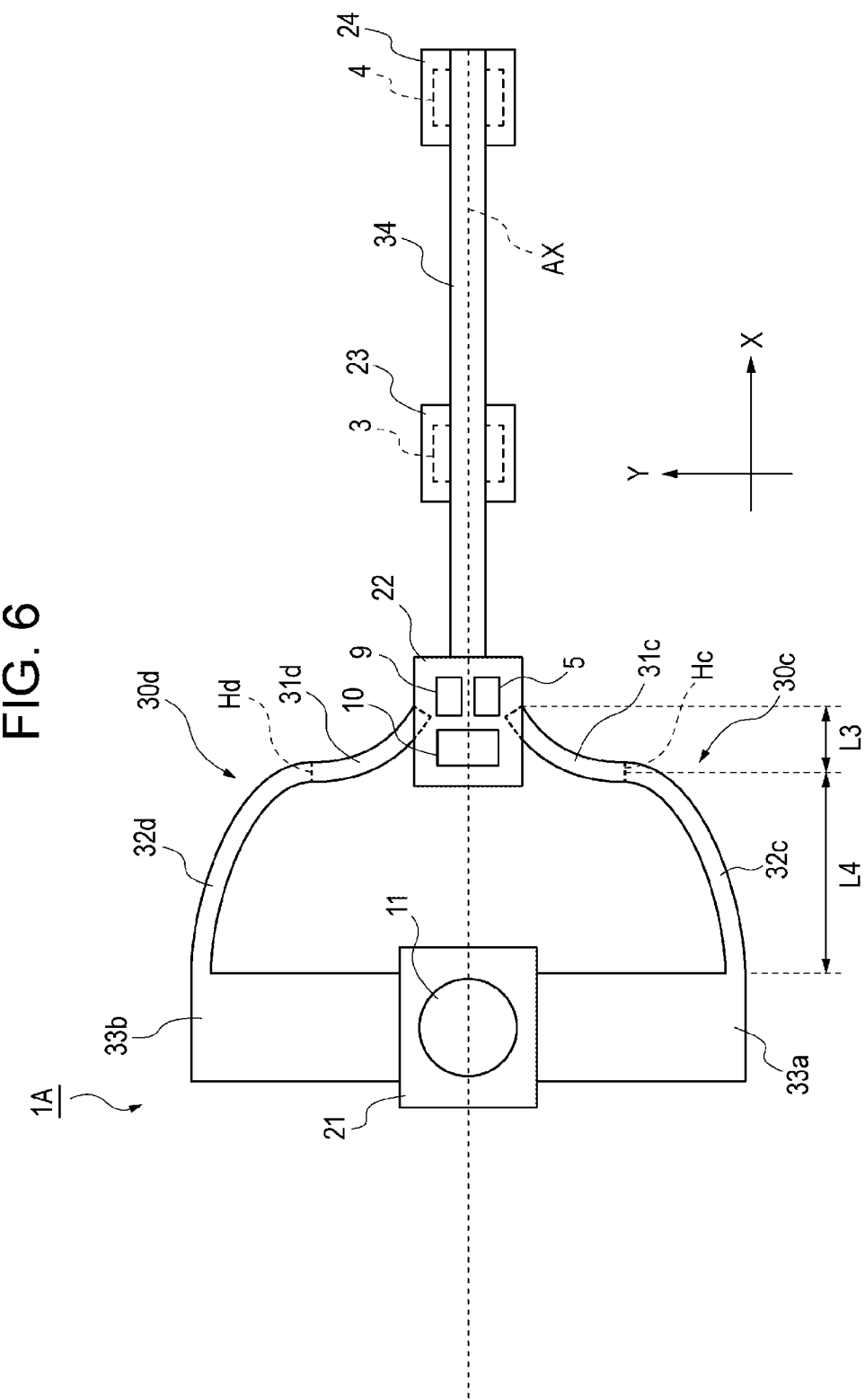
FIG. 6 is a development view of a probe circuit section in a reference example.

Next, a probe circuit section 1A in a reference example will be described with reference to FIGS. 6, 7A, and 7B. FIG. 6 is a development view of the probe circuit section 1A in the reference example, FIG. 7A is a view of the probe circuit section 1A in a state where the finger F is bent, as seen from the lateral side, and FIG. 7B is a view of the probe circuit section 1A illustrated in FIG. 7A, as seen from the upper side.

As illustrated in FIG. 6, the probe circuit section 1A is different in a first arm portion 30c and a second arm portion 30d from the probe circuit section 1 (see FIG. 3) in the embodiment. The first arm portion 30c has a first arcuate portion 31c and a second arcuate portion 32c. The first arcuate portion 31c is arcuate toward the mounting portion 21, and connected to the mounting portion 22. The second arcuate portion 32c is arcuate so as to separate from the mounting portion 21, and connected to the first connecting portion 33a. The first arcuate portion 31c is formed integrally with the second arcuate portion 32c. The borderline Hc between the first arcuate portion 31c and the second arcuate portion 32c is the inflection point of the curve of the first arm portion 30c. In the X-axis direction, the length L3 of the first arcuate portion 31c is shorter than the length L4 of the second arcuate portion 32c.

The second arm portion 30d has a first arcuate portion 31d and a second arcuate portion 32d. The first arcuate portion 31d is arcuate toward the mounting portion 21, and connected to the mounting portion 22. The second arcuate portion 32d is arcuate so as to separate from the mounting portion 21, and connected to the second connecting portion 33b. The first arcuate portion 31d is formed integrally with the second arcuate portion 32d. The borderline Hd between the first arcuate portion 31d and the second arcuate portion 32d is the inflection point of the curve of the second arm portion 30d. In the X-axis direction, the length of the first arcuate portion 31d is shorter than that of the second arcuate portion 32d.

As illustrated in FIG. 7, in the case where the distal and proximal interphalangeal joints of the finger F are bent, next, the first arm portion 30c and second arm portion 30d of the probe circuit section 1A largely expand toward the outside of the probe circuit section 1A. In the X-axis direction, namely, the length L3 of the first arcuate portion 31c is shorter than the length L4 of the second arcuate portion 32c, and therefore the first arm portion 30c largely expands so as to separate from the finger F, in the case where the distal and proximal interphalangeal joints of the finger F are bent. In the X-axis direction, similarly, the length of the first arcuate portion 31d is shorter than that of the second arcuate portion 32d, and therefore the second arm portion 30d largely expands toward the outside of the probe circuit section 1A, in the case where the distal and proximal interphalangeal joints of the finger F are bent.

In the embodiment, in the X-axis direction, by contrast, the length of the first arcuate portion 31a (or the first arcuate portion 31b) is longer than that of the second arcuate portion 32a (or the second arcuate portion 32b) as described above. Therefore, it is possible to preferably prevent the first arm portion 30a (the second arm portion 30b) from largely expanding so as to separate from the finger F, even in the case where the distal and proximal interphalangeal joints of the finger F are bent.

Although the embodiment of the invention has been described, the technical scope of the invention should not be limitedly interpreted by the description of the embodiment. It should be understood by those skilled in the art that the embodiment is a mere example, and may be variously changed within the scope of the invention as defined in the claims. The technical scope of the invention should be determined based on the scope of the invention as defined in the claims, and the scope of equivalence thereof. For example at least one of first arcuate portion 31a and second arcuate portion 32b can be formed curve, bend or other nonlinear.

In FIG. 3, for example, the two arm portions or the first arm portion 30a and the second arm portion 30b are disposed. Alternatively, only one of the first arm portion 30a and the second arm portion 30b may be disposed. In the alternative, there is only one arm portion, and therefore the possibility that, in a state where the probe 100 is attached to the patient, the arm portion is in contact with a peripheral article can be further lowered. As described above, the usability of the probe 100 can be improved.

What is claimed is:

1. A pulse photometry probe which is to be attached to a living tissue of a subject, comprising:
   a light emitter that emits a light beam toward the living tissue of the subject;
   a light detector that receives the light beam emitted from the light emitter and passing through the living tissue, to produce a vital signal;
   a vital data acquiring section that acquires vital data of the subject based on the vital signal;
   a wireless communicating section that wirelessly transmits the vital data;
   a first mounting portion that is electrically connected to the vital data acquiring section and the wireless communicating section, and on which a power source section for supplying electric power is mounted;
   a second mounting portion on which the vital data acquiring section and the wireless communicating section are mounted;
   a first arm portion that electrically connects the first mounting portion and the second mounting portion to each other and
   a second arm portion that electrically connects the first mounting portion and the second mounting portion to each other,
   wherein the first arm portion and second arm portion do not overlap, and a gap is located between the first arm portion and the second arm portion, and
   wherein the first arm portion and second arm portion each comprise a respective nonlinear portion and a respective inflection point.

2. The probe according to claim 1, wherein the vital data acquiring section includes:
   an AD converting section that converts the vital signal to a digital signal; and
   a controller that acquires the vital data based on the digital signal.

3. The probe according to claim 1 further comprising:
   a third mounting portion on which the light emitter is mounted; and
   a fourth mounting portion on which the light detector is mounted,
   the second mounting portion and the third mounting portion are electrically connected to each other, and
   the second mounting portion and the fourth mounting portion are electrically connected to each other.

4. The probe according to claim 3 wherein
   the living tissue is a portion of a finger, and
   in an insertion direction along which the living tissue is inserted into the probe, a length from the second mounting portion to each respective inflection point is equal to or longer than a length from the respective inflection point to the first mounting portion.

5. The probe according to claim 4, wherein
   the second arm portion is opposed to the first arm portion in a direction perpendicular to the insertion direction, and
   the first arm portion and the second arm portion are symmetrical with each other about an axis which passes through a center of the second mounting portion, and which is parallel to the insertion direction.

6. The probe according to claim 2 further comprising:
   a third mounting portion on which the light emitter is mounted; and
   a fourth mounting portion on which the light detector is mounted,
   the second mounting portion and the third mounting portion are electrically connected to each other, and
   the second mounting portion and the fourth mounting portion are electrically connected to each other.

7. The probe according to claim 6 wherein
   the living tissue is a portion of a finger, and
   in an insertion direction along which the living tissue is inserted into the probe, a length from the second mounting portion to each respective inflection point is equal to or longer than a length from the respective inflection point to the first mounting portion.

8. The probe according to claim 7, wherein
   the second arm portion is opposed to the first arm portion in a direction perpendicular to the insertion direction, and
   the first arm portion and the second arm portion are symmetrical with each other about an axis which passes through a center of the second mounting portion, and which is parallel to the insertion direction.

9. The probe according to claim 1, wherein the first mounting portion is a first circuit board and the second mounting portion is a second circuit board.

10. The probe according to claim 1, wherein the first mounting portion and the second mounting portion are electrically connected via the respective nonlinear portion s of the first arm portion and second arm portion.

11. The probe according to claim 1, wherein the first mounting portion and the second mounting portion are movable relative to each other.

12. A pulse photometry probe which is to be attached to a portion of a finger of a subject, comprising:
   a light emitter that emits a light beam toward the portion of the finger;
   a light detector that receives the light beam emitted from the light emitter and passing through the portion of the finger, to produce a vital signal;
   a vital data acquiring section that acquires vital data of the subject based on the vital signal;
   a wireless communicating section that wirelessly transmits the vital data;
   a first mounting portion that is electrically connected to the vital data acquiring section and the wireless communicating section, and on which a power source section for supplying electric power is mounted;
   a second mounting portion on which the vital data acquiring section and the wireless communicating section are mounted;

a first arm portion that electrically connects the first mounting portion and the second mounting portion to each other and a second arm portion that electrically connects the first mounting portion and the second mounting portion to each other, wherein the first arm portion and second arm portion do not overlap, and a gap is located between the first arm portion and the second arm portion wherein the first arm portion and second arm portion each comprise a respective nonlinear portion and a respective inflection point, and wherein in an insertion direction along which the portion of the finger is inserted into the probe, a length from the second mounting portion to each respective inflection point is equal to or longer than a length from the respective inflection point to the first mounting portion.

13. A pulse photometry probe which is to be attached to a living tissue of a subject, comprising:
- a light emitter that emits a light beam toward the living tissue of the subject;
- a light detector that receives the light beam emitted from the light emitter and passing through the living tissue, to produce a vital signal;
- a controller that acquires vital data of the subject based on the vital signal;
- a wireless communicating section that wirelessly transmits the vital data;
- a first mounting portion that is electrically connected to the controller and the wireless communicating section, and on which a power source section for supplying electric power is mounted;
- a second mounting portion on which the controller and the wireless communicating section are mounted;
- a first arm portion that electrically connects the first mounting portion and the second mounting portion to each other and
- a second arm portion that electrically connects the first mounting portion and the second mounting portion to each other,
- wherein the first arm portion and second arm portion do not overlap, and a gap is located between the first arm portion and the second arm portion,
- wherein the first arm portion and second arm portion each comprise a respective nonlinear portion and a respective inflection point.

14. The probe according to claim 13, wherein the first mounting portion is a first circuit board and the second mounting portion is a second circuit board.

15. The probe according to claim 13, wherein the first mounting portion and the second mounting portion are electrically connected via the respective nonlinear portion s of the first arm portion and second arm portion.

16. The probe according to claim 13, wherein the first mounting portion and the second mounting portion are movable relative to each other.

* * * * *